(12) United States Patent
Paszicsnyek

(10) Patent No.: US 12,048,556 B2
(45) Date of Patent: Jul. 30, 2024

(54) SYSTEM AND METHOD FOR AIDING IN PHYSIOTHERAPY BY MEASURING MUSCLE ACTIVITY USING WIRELESS SENSORS

(71) Applicant: InBOS GmbH, Kapfenberg (AT)

(72) Inventor: Thomas Paszicsnyek, bruck/Mur (AT)

(73) Assignee: InBOS GmbH, Kapfenberg (AT)

( * ) Notice: Subject to any disclaimer, the term of this patent is extended or adjusted under 35 U.S.C. 154(b) by 492 days.

(21) Appl. No.: 17/482,028

(22) Filed: Sep. 22, 2021

(65) Prior Publication Data

US 2022/0087598 A1 Mar. 24, 2022

Related U.S. Application Data

(60) Provisional application No. 63/081,382, filed on Sep. 22, 2020.

(51) Int. Cl.
| | |
|---|---|
| *A61B 5/00* | (2006.01) |
| *A61B 5/11* | (2006.01) |
| *A61B 5/256* | (2021.01) |
| *A61B 5/296* | (2021.01) |
| *A61B 5/397* | (2021.01) |
| *G16H 20/30* | (2018.01) |

(52) U.S. Cl.
CPC .......... *A61B 5/4528* (2013.01); *A61B 5/1107* (2013.01); *A61B 5/256* (2021.01); *A61B 5/296* (2021.01); *A61B 5/397* (2021.01); *A61B 5/4848* (2013.01); *A61B 5/6804* (2013.01); *G16H 20/30* (2018.01); *A61B 2505/09* (2013.01)

(58) Field of Classification Search
CPC . A61B 2505/09; A61B 5/0022; A61B 5/1107; A61B 5/1114; A61B 5/256; A61B 5/296; A61B 5/397; A61B 5/4528; A61B 5/4848; A61B 5/6804; G16H 20/30; G16H 40/40; G16H 40/67; G16H 50/20; G16H 50/70
See application file for complete search history.

(56) References Cited

U.S. PATENT DOCUMENTS

2011/0208444 A1* 8/2011 Solinsky ............... A61B 5/1114
702/41

* cited by examiner

*Primary Examiner* — George Manuel
(74) *Attorney, Agent, or Firm* — Meister Seelig & Fein PLLC

(57) ABSTRACT

A method and system for determining rehabilitation treatment of a joint, the method comprising communicatively connecting to a plurality of sensors attached to an individual at muscles in a joint area, wherein the plurality of sensors transmit electrical signals generated by the muscle to the computing device. The method further comprising receiving the electrical signals from the plurality of sensors, generating initial measurement data by evaluating strength and activity level of the muscles based on the electrical signals, and comparing the initial measurement data with reference data, wherein the reference data includes measurements of healthy people with normal muscle function. The method further comprising generating a training plan based on the comparison.

20 Claims, 11 Drawing Sheets

FIG. 4

SYSTEM AND METHOD FOR AIDING IN PHYSIOTHERAPY BY MEASURING MUSCLE ACTIVITY USING WIRELESS SENSORS

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

CROSS REFERENCE TO RELATED APPLICATION

This application claims the priority of U.S. Provisional Application No. 63/081,382, entitled "SYSTEM AND METHOD FOR AIDING IN PHYSIOTHERAPY BY MEASURING MUSCLE ACTIVITY USING WIRELESS SENSORS," filed on Sep. 22, 2020, the disclosure of which is hereby incorporated by reference in its entirety.

BACKGROUND OF THE INVENTION

Field of the Invention

This application generally relates to testing muscle structures, and in particular, determining muscle activity of an affected to create a rehabilitation plan.

Description of the Related Art

As the population increasingly grows older, the number of people suffering from debilitating conditions resulting from muscular skeletal injuries and degenerative diseases increases. Rehabilitative care and physical therapy can substantially treat these conditions and improve quality of life. A doctor may also refer patients to physical therapy after surgery, such as a hip or knee replacement. Physical therapy may address the limitations of a person's ability to move and perform functional activities in their daily lives.

There is no currently available medical diagnostic apparatus or methodology, which, as it relates to various body regions including spine, shoulder, elbow, wrist, hip, knee, ankle, and foot, allows for objective quantification of an individual's orthopedic movement function and/or physical therapy dysfunction. Additionally, there is no available apparatus or methodology that is capable of comparing the severity of dysfunction of the various body regions of a patient to a norm; nor is there any routine available that allows for the objective measurement of the patient management process to include progression or improvement from pre- to postoperative status.

SUMMARY OF THE INVENTION

The present invention provides a method, system, and non-transitory computer readable media for determining rehabilitation treatment of a joint. According to one embodiment, the method comprises communicatively connecting to a plurality of sensors attached to an individual at muscles in a joint area, wherein the plurality of sensors transmit electrical signals generated by the muscle to the computing device. The method further comprises receiving the electrical signals from the plurality of sensors, generating initial measurement data by evaluating strength and activity level of the muscles based on the electrical signals, and comparing the initial measurement data with reference data, wherein the reference data includes measurements of healthy people with normal muscle function. The method further comprises generating a training plan based on the comparison.

The method further comprises measuring electrical signals generated by muscle cell activation. The plurality of sensors may include sleeves with inwoven electromyographic sensors. The plurality of sensors may include gyrosensors that are placed at a beginning and at an end of the sleeve. The plurality of sensors may be placed according to a beginning and an end of defined muscles in a joint area.

Comparing the initial measurement data with reference data may further comprise determining a target zone associated with the training plan. The training plan may include training procedures including progress and exercises to be performed along with explanations or descriptions. The training plan may include an exercise list and a target zone based on average data of a healthy cohort. The method may further comprise continuously adapting the training plan according to individual joint progress and abilities. In one embodiment, calibration procedures are executed with the plurality of sensors by instructing through a user interface, a user to perform operations including at least one of moving forward and backward, flexing and extending a joint attached to the plurality of sensors, and rotating the joint.

According to one embodiment, the system comprises a processor and a memory having executable instructions stored thereon that when executed by the processor cause the processor to communicatively connect to a plurality of sensors attached to an individual at muscles in a joint area. The processor is configured to receive electrical signals generated by the muscle from the plurality of sensors, generate initial measurement data by evaluating strength and activity level of the muscles based on the electrical signals, and compare the initial measurement data with reference data. The reference data includes measurements of healthy people with normal muscle function. The processor is further configured to generate a training plan based on the comparison.

The plurality of sensors may measure electrical signals generated by muscle cell activation. The plurality of sensors may include sleeves with inwoven electromyographic sensors. The plurality of sensors may include gyrosensors that are placed at a beginning and at an end of the sleeve. The plurality of sensors may be placed according to a beginning and an end of defined muscles in a joint area.

The processor may be further configured to determine a target zone associated with the training plan. The processor may be further configured to execute calibration procedures with the plurality of sensors by instructing through a user interface, a user to perform operations including at least one of moving forward and backward, flexing and extending a joint attached to the plurality of sensors, and rotating the joint. The training plan may include an exercise list and a target zone based on average data of a healthy cohort. The processor may be further configured to continuously adapting the training plan according to individual joint progress and abilities.

According to one embodiment, the non-transitory computer-readable media comprises program code that when executed by a programmable processor causes execution of a method for determining rehabilitation treatment of a joint. The computer-readable media comprises computer program code for communicatively connecting a computing device to a plurality of sensors attached to an individual at muscles in a joint area, wherein the plurality of sensors transmit electrical signals generated by the muscle to the computing device. The computer-readable media further comprises computer program code for receiving the electrical signals from the plurality of sensors, computer program code for generating initial measurement data by evaluating strength and activity level of the muscles based on the electrical signals, and computer program code for comparing the initial measurement data with reference data, wherein the reference data includes measurements of healthy people with normal muscle function. The computer-readable media further comprises computer program code for generating a training plan based on the comparison.

BRIEF DESCRIPTION OF THE DRAWINGS

The invention is illustrated in the figures of the accompanying drawings which are meant to be exemplary and not limiting, in which like references are intended to refer to like or corresponding parts.

FIGS. 4 through 10 illustrate exemplary interfaces of a surgical planning and evaluation system according to an embodiment of the present invention.

DETAILED DESCRIPTION OF THE INVENTION

Figure 1:
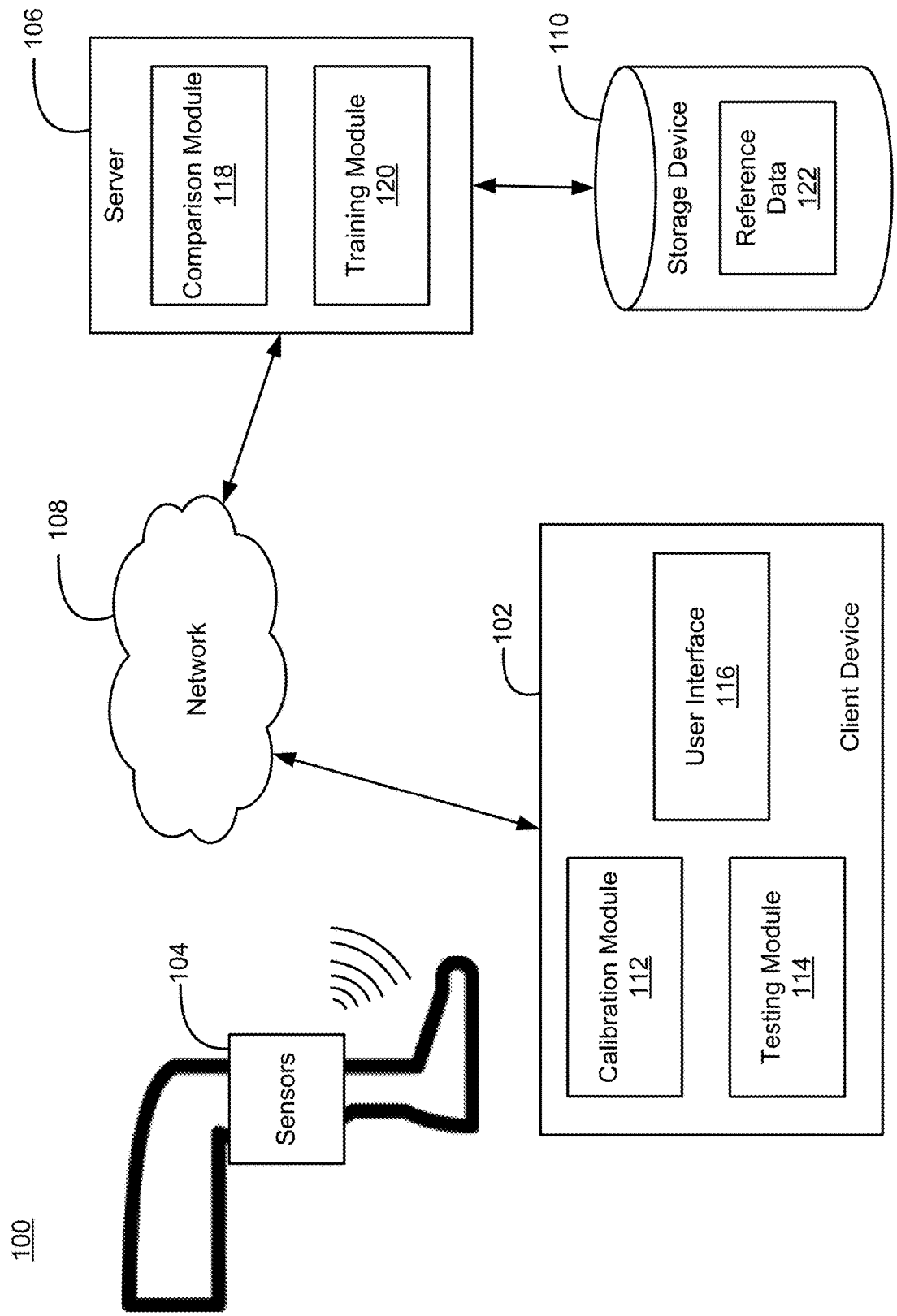
FIG. 1 illustrates a computing system according to an embodiment of the present invention.

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

The present application discloses a system that measures the present status of muscular and coordinate ability and creates a rehabilitation training plan based on measurements of muscle activity of an affected joint. The measurements may be compared to normal muscle activities of the muscle envelope in combination with a gait analysis and movement evaluation. Measurement procedures may take place in a surgeon's office and at the beginning of therapy and can be repeated during a variety of exercises. In case of surgery, a preoperative data assessment may also be performed to establish a baseline and to value the overall condition in relation to muscle activity and coordinate ability, as well as the biomedical individual movement of the different joints. The system may include sleeves with inwoven electromyographic ("EMG") sensors, which are placed according to a beginning and end of defined muscles in a joint area, and gyrosensors, which are placed at the beginning and end of the sleeve. The sleeves may be worn on both sides of the upper or lower extremities or as shirt for measuring the vertebral column. Measurement data from the sensor may be wirelessly transmitted (e.g., Bluetooth) to a software application executing on a client device.

The disclosed system may be used for physiotherapeutical treatments regarding conservative and operative treatment of, for example, major joints and the vertebral column. The system may further include a database of reference data of healthy people with normal muscle function. By comparing the measurements with the database, a target zone may be determined with respect to a kind of physical therapy regimen (surgery, conservative, or general condition improvement). To reach this target zone, measurement data from the sensors may be displayed on the client device and necessary training of the correct muscle structures may be identified based on the measurement data. As such, training procedures may be presented (e.g., different screens including progress and exercises to be performed along with explanations or descriptions) on the client device and can be performed under surveillance of a treating doctor, physiotherapist, or by patients themselves. According to one embodiment, the database and training procedures may be accessible through a client application connected to a cloud-based service.

FIG. 1 presents a computing system according to an embodiment of the present invention. The system 100 presented in FIG. 1 includes client device 102, sensors 104, server 106, network 108, and storage device 110. Client device 102 may comprise a computing device (e.g., desktop computer, television device, laptop, personal digital assistant (PDA), smartphone, tablet computer, e-book reader, smart watch and smart wearable devices, or any computing device having a central processing unit and memory unit capable of connecting to a network). The client device 102 may also comprise a graphical user interface (GUI) or a browser application provided on a display (e.g., monitor screen, LCD or LED display, projector, etc.). Client device 102 may include or execute a variety of operating systems, including a personal computer operating system, such as a Windows, Mac OS or Linux, or a mobile operating system, such as iOS, Android, or Windows Phone, or the like. The client device 102 may include or may execute a variety of possible applications, such as a client software application enabling communication with other devices.

Sensors 104 may comprise fabric sleeves or stockings with inwoven EMG sensors that measure electrical signals generated by muscle cells when electrically or neurologically activated. The electrical signals can be analyzed to detect abnormalities or used to analyze biomechanical movement. The sensors 104 may be placed according to a tested joint near a beginning and ending of a key muscle structure. According to one embodiment, a pair of sleeves including the sensors 104 may be worn one for each muscle (e.g., one for each anatomical left and right body part pair). As such, a comparison may be made of the individual situation within the patient. The sensors 104 may communicate the signals to client device 102 via a wireless communication connection, such as by Bluetooth, Wi-Fi, or near-field communication (NFC). The signals from sensors 104 may be stored on client device 102 and compared to data provided by server 106. Specifically, comparative data (e.g., reference data of healthy people with normal muscle function) from a reference data 122 stored in storage device 110 may be accessed by client device 102 through server 106 over network 108, for example, as a cloud-based service, or a service subscription.

Client device may include a calibration module 112, testing module 114, and user interface 116. Calibration module 112 may include logic for executing calibration procedures with the sensors 104 by instructing a user through user interface 116 to perform several operations such as, moving forward and backward, flexing and extending a joint attached to the sensor, or rotating the joint. The calibration module 112 may ensure consistent measurement results that can be compared to reference data 122 by positioning the sensors 104 or mapping the results they provide. Testing module 114 may include testing protocols for measuring or evaluating the strength and activity level of key muscle structures of the joint measured by the sensors 104. An initial measurement data gathered by testing module 114 may be transmitted to a comparison module 118 at server 106 where comparison module 118 may compare the initial measurement data with reference data 122. The reference data 122 may include measurements from healthy people with normal muscle function. According to the data acquired via initial measurement, an evaluation of movement behavior can be visualized by generating a virtual avatar of involved regions. Based on the comparison, training module 120 may generate a training plan and transmit the training plan to user interface 116. The initial measurement data, its comparison, and the training plan may presented to a user interface and/or transferred to any kind of wearable augmented reality device for viewing.

Server 106, as described herein, may vary widely in configuration or capabilities but is comprised of at least a special-purpose digital computing device including at least one or more central processing units and memory. The server 106 may also include one or more of mass storage devices, power supplies, wired or wireless network interfaces, input/output interfaces, and operating systems, such as Windows Server, Mac OS X, Unix, Linux, FreeBSD, or the like. In an example embodiment, server 106 may include or have access to memory for storing instructions or applications for the performance of various functions and a corresponding processor for executing stored instructions or applications. For example, the memory may store an instance of the server 106 configured to operate in accordance with the disclosed embodiments.

Network 108 may be any suitable type of network allowing transport of data communications across thereof. The network 108 may couple devices so that communications may be exchanged, such as between servers and client devices or other types of devices, including between wireless devices coupled via a wireless network, for example. Network 108 may also include mass storage, such as network attached storage (NAS), a storage area network (SAN), cloud computing and storage, or other forms of computer or machine readable media, for example. In one embodiment, the network may be the Internet, following known Internet protocols for data communication, or any other communication network, e.g., any local area network (LAN) or wide area network (WAN) connection, cellular network, wire-line type connections, wireless type connections, or any combination thereof. Communications and content stored and/or transmitted to and from client device 102 may be encrypted using, for example, the Advanced Encryption Standard (AES) with a 128, 192, or 256-bit key size, or any other encryption standard known in the art.

According to another embodiment, the system may further include additional equipment to gather information such as, gait analysis, load distribution analysis, and motion analysis. Exemplary equipment may include special cameras and insoles employed to gather the information. For example, gait analysis, load distribution analysis, and motion analysis may include monitoring data from insoles worn by an individual and capturing movement during a walking procedure, treadmills, and load platforms.

Figure 2:
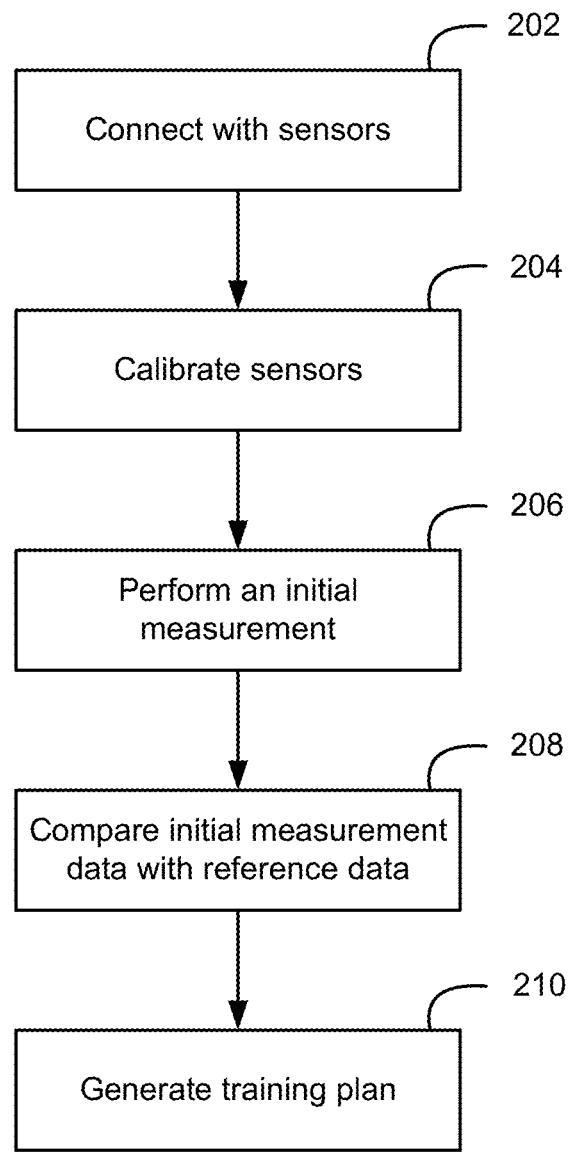
FIG. 2 illustrates a flowchart of a method for determining rehabilitation treatment of a joint based on muscle activity according to an embodiment of the present invention.

FIG. 2 presents a flowchart of a method for determining rehabilitation treatment of a joint based on muscle activity according to an embodiment of the present invention. Sensors may be worn or placed at a pair of given muscle groups or joints of an individual being treated. A client device is connected with sensors, step 202. Connecting the client device with the sensors may include a pairing procedure. For example, a button on a given sensor may be pressed to cause a light on the sensor to flash blue indicating initiation of device pairing. Then on the client device, a pairing number or identifier may be entered into an interface to pair with the sensor. Upon successfully connecting with the sensor, the light on the sensor may change to green.

The sensors are calibrated, step 204. The client device may calibrate the sensors by instructing a user to perform several operations such as, moving forward and backward, flexing and extending a joint attached to the sensor, or rotating the joint. The client device may display an indicator, e.g., a green bar, to indicate that a calibration of the sensors was successful.

An initial measurement is started, step 206. The initial measurement may include an initial testing protocol, which evaluates the basic strength and activity level of the key muscle structures of the joint measured by the sensors. Initial measurement data may be generated based on the evaluation. The sensors may be attached to an individual at muscles in a joint area and transmit electrical signals generated by the muscles to the client device. In the case of surgery, the testing protocol may also be repeated after surgery to compare pre- and postoperative status. The testing protocol may comprise a series of exercises during which measurements based on data from the sensors can be recorded. The user may be instructed to, for example, walk on a treadmill, walk up and down stairs, sit down and stand up, and fully flex and extend a joint. Upon performing the initial measurement, an interface on the client device may display results including muscle strength, comparison of a healthy and an affected side, and range of motion.

The initial measurement data is compared with reference data, step 208. The reference data may include measurements from healthy people with normal muscle function. A training plan is generated based on the comparison, step 210. The training plan may include an exercise list along with a target zone based on average data of a healthy cohort. An interface may be presented with the training plan indicating exercise status (e.g., orange—not yet performed, green— completed, red—performed incorrectly) and a target zone achievement indicator. The training plan may be continuously adapted to individual joint progress and abilities. In case of guided therapy, the training plan may be given to the treating persons (physiotherapist, doctors) and may be approved or changed especially in case of surgery that changes loads and range of motion of joints. The interface may further include a result screen that may show trend per day/week/month/year, reports (e.g., daily, weekly, monthly), summary and recommendations, summary of the success, recommendations to improve outcome, and a button for uploading contents to the interface.

Figure 3:
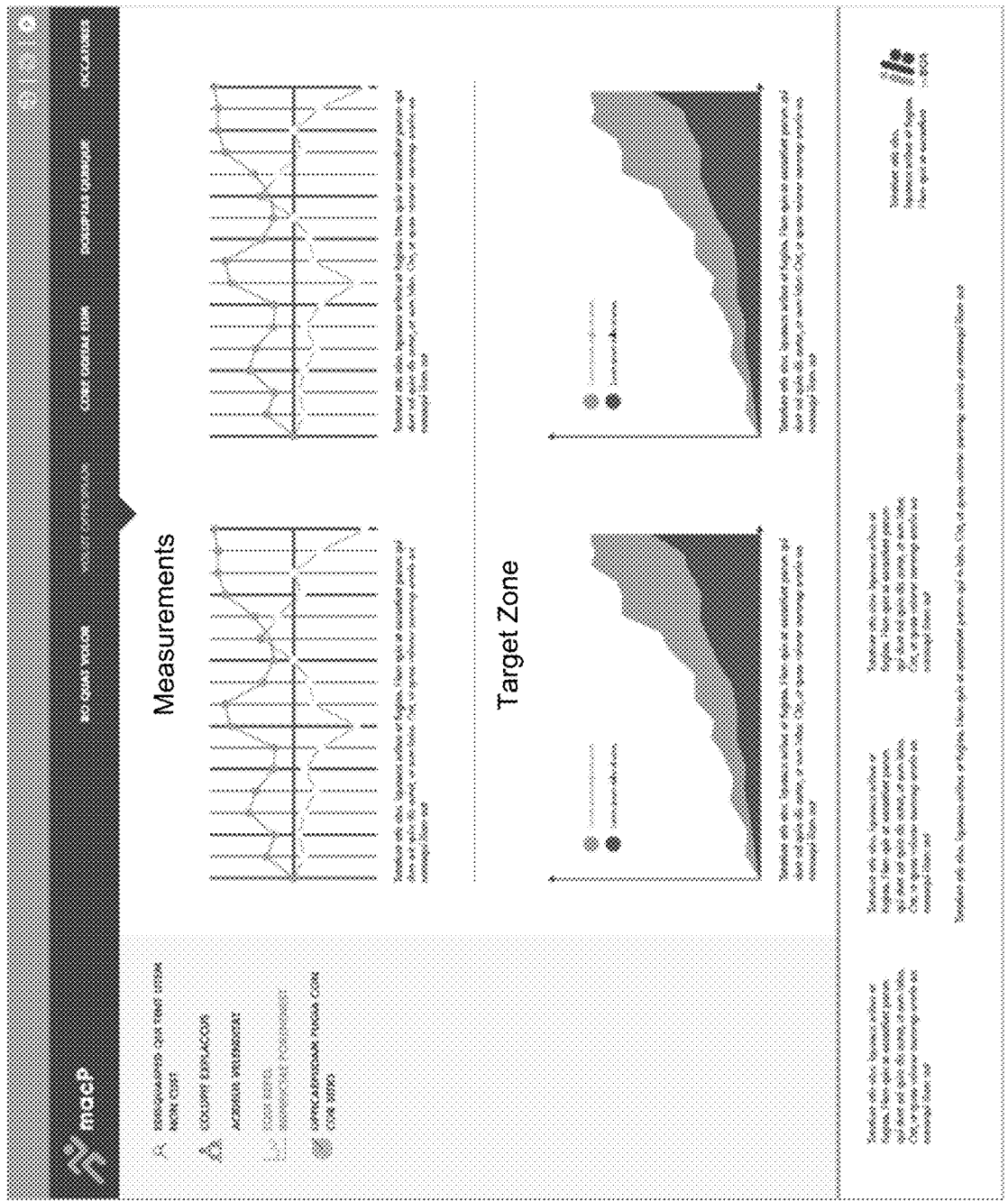
FIG. 3 illustrates an exemplary training plan interface according to an embodiment of the present invention.

FIG. 3 presents an exemplary training plan interface according to an embodiment of the present invention. The interface may include the results of the measurements as well as the recommendations the patient of physiotherapist should follow. Trends and results may also be displayed on the interface.

Figure 4:
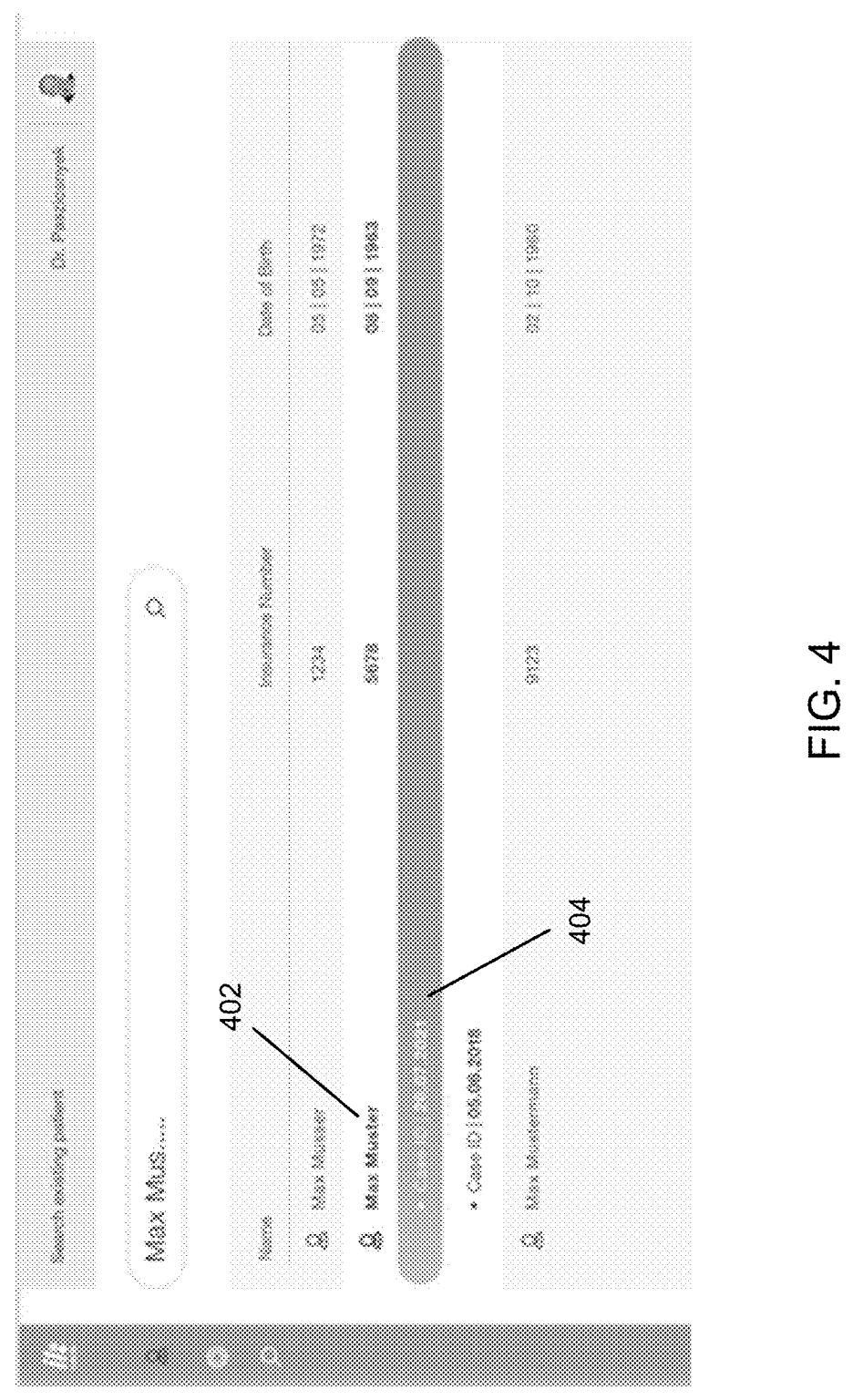
Figure 5:
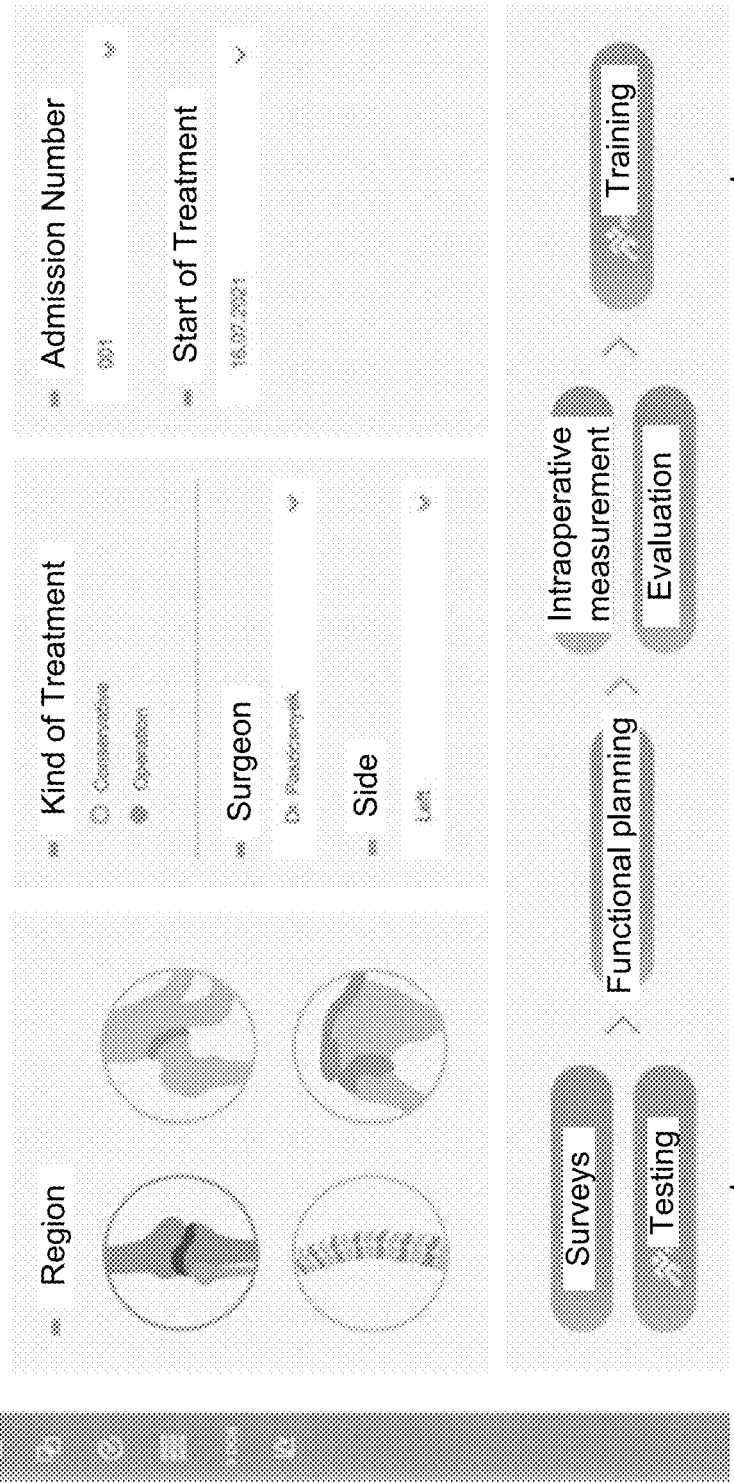

The disclosed system may be used to monitor patient progress after surgery and to guide physiotherapy. FIGS. 4 through 10 present exemplary interfaces of a surgical planning and evaluation system according to an embodiment of the present invention. Referring to FIGS. 4 and 5, a case 404 may be stored to a patient profile 402 for planning one or more treatment phases 502. The treatment phases 502 may include surveys, testing, functionality planning, interoperative measurement and/or evaluation, and physiotherapy training. The case 404 may further include representative graphics of operating regions and information including kind of treatment (e.g., conservative or operation), surgeon, side, admission number, and starting date of treatment.

Figure 6:
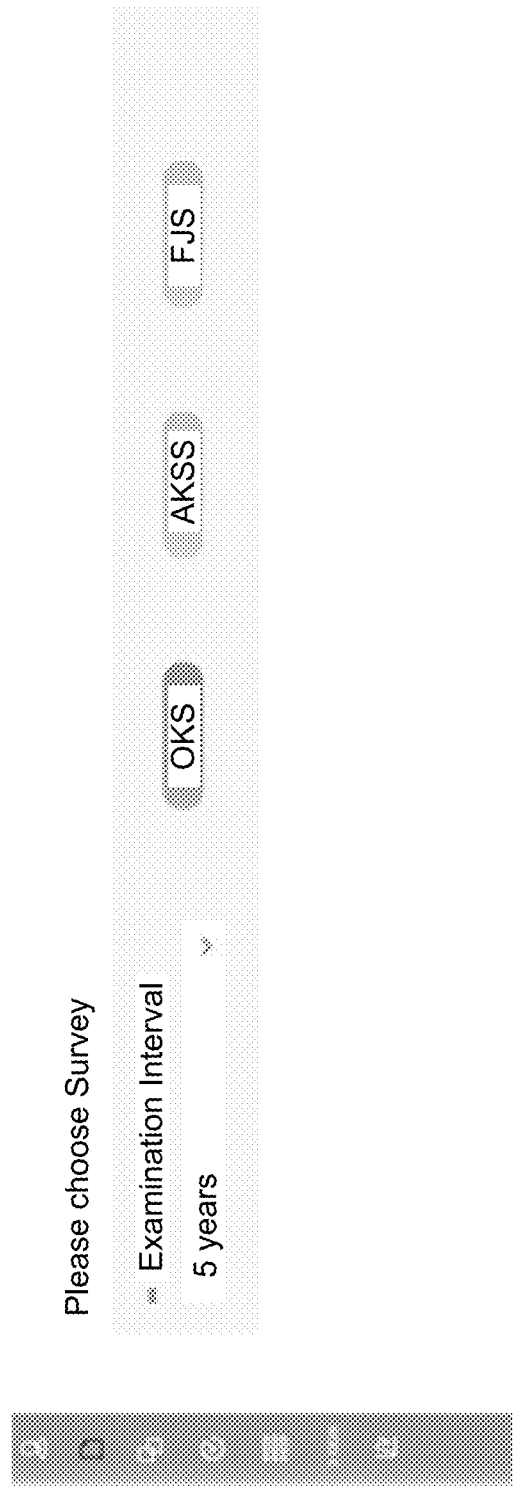
Figure 7:
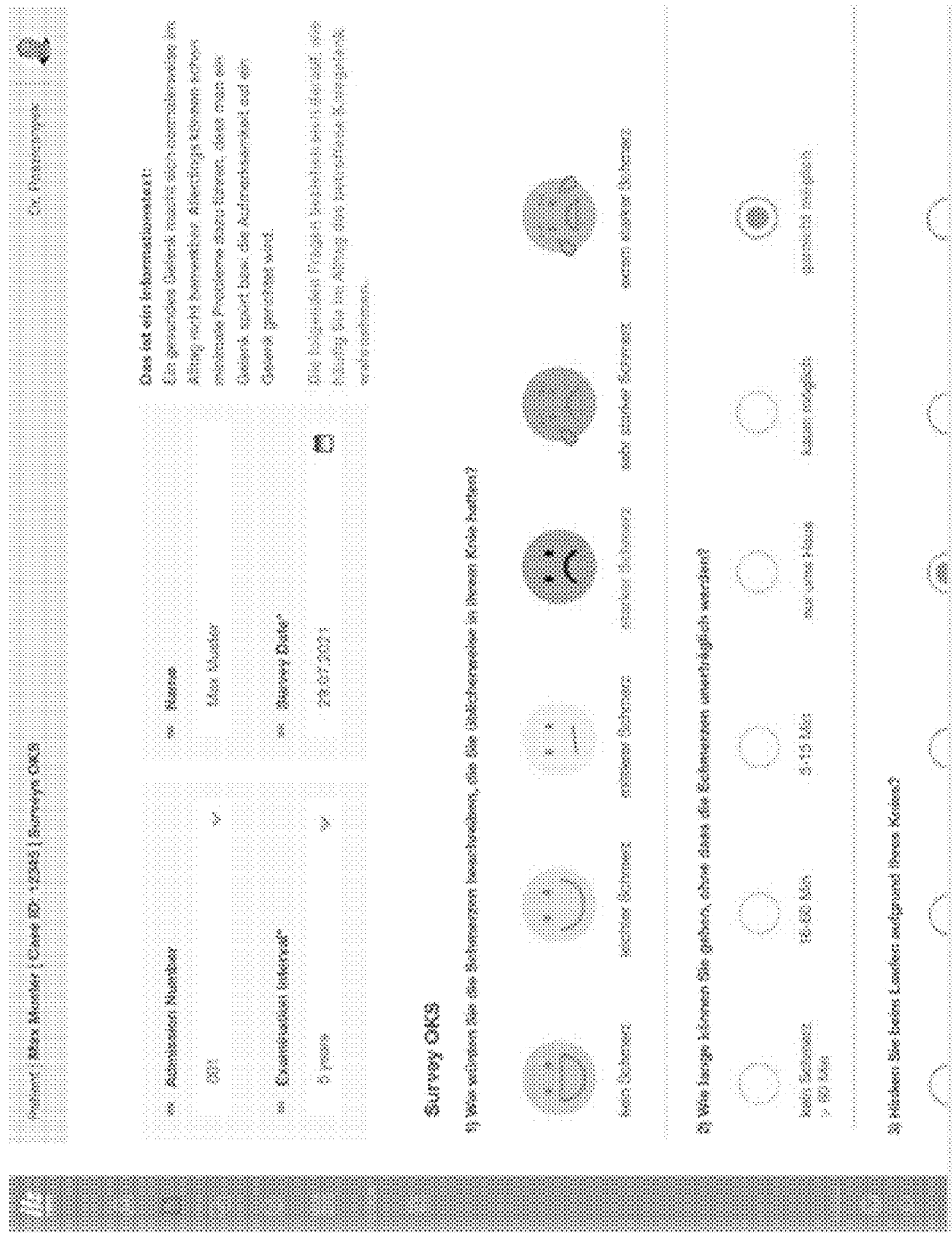

Referring to FIGS. 6 through 7, surveys may be saved to a patient profile 402 for recording preferences, lifestyles (e.g., current activities and capabilities) and demands (e.g., desired kinds of activities and capabilities) relating to the surgery. Exemplary surveys may include Oxford Knee Score ("OKS"), American Knee Society Score ("AKSS"), and Forgotten Joint Score ("FJS").

Figure 8:
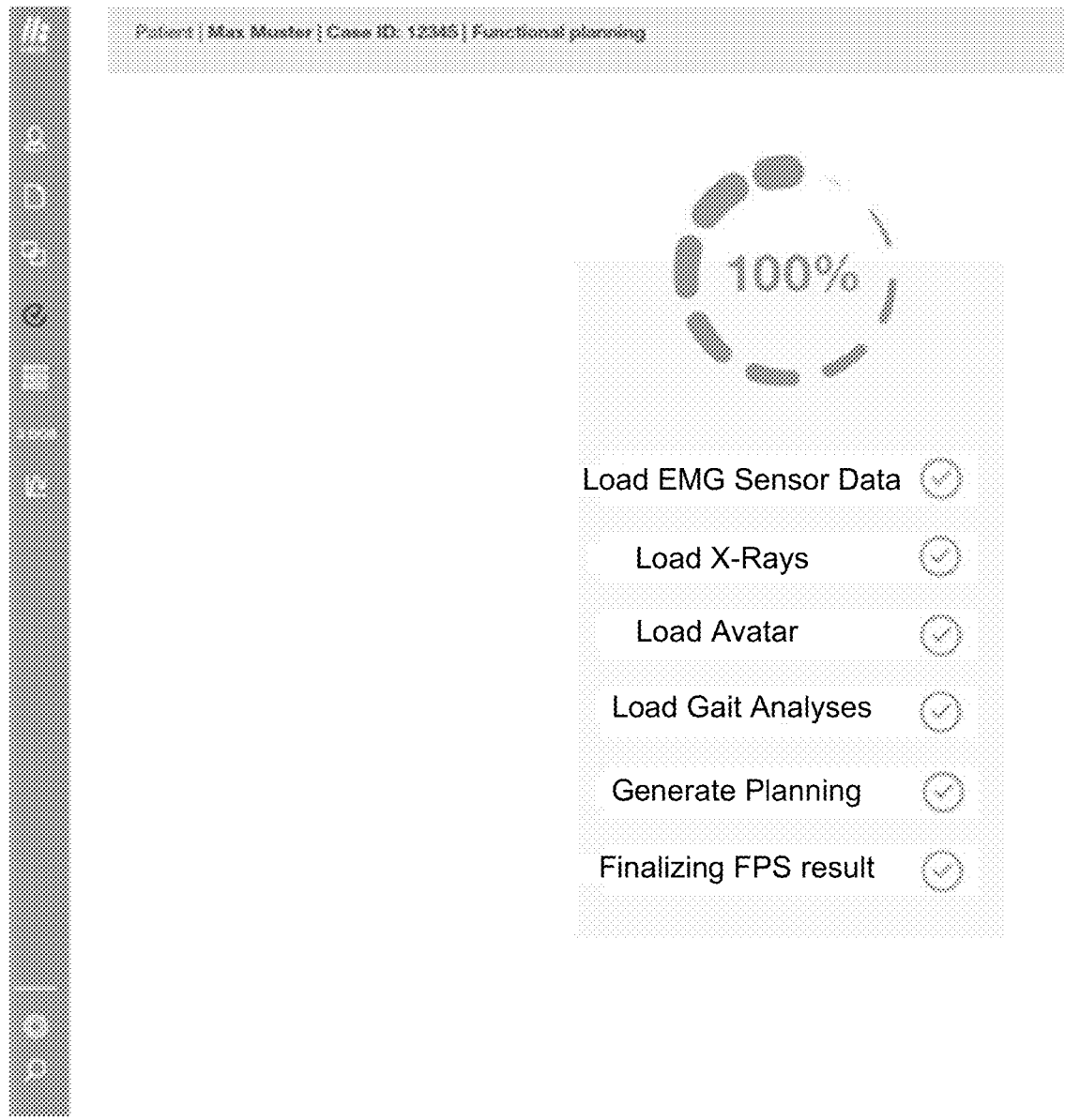
Figure 9:
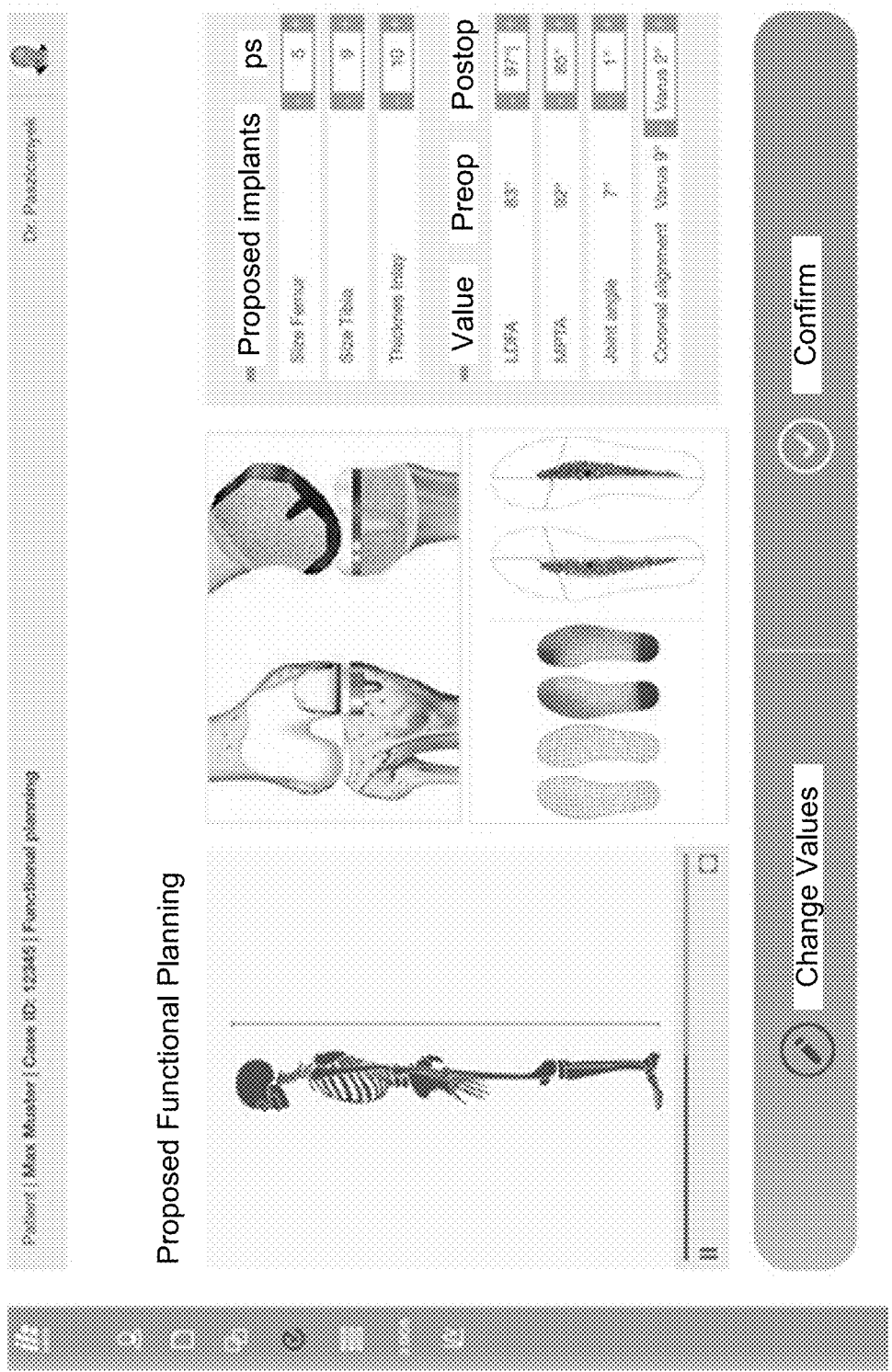

Referring to FIG. 8, several data sets such as, sensor data X-Rays, gait analyses, load distribution analysis, and motion analysis may be loaded to the surgical planning and evaluation system. Based on the data sets, the surgical planning and evaluation system may generate functional planning data including preoperative and postoperative joint stability and functionality, and recommended implant sizes to achieve joint replacement that is satisfactory in performance. The surgical planning and evaluation system may generate a user interface including avatars, graphics, recommendations, and data values based on the data sets and functional planning data, as illustrated in FIG. 9. Avatars representative of a patient and operating regions with proposed implants may be presented on the user interface. Recommendations may comprise proposed implants may be generated, e.g., size femur, size tibia, and thickness inlay. Values presented on the user interface may include pre-operation and post-operation values for lateral distal-femoral angle (LDFA), medial proximal tibial angle (MPTA), joint angle, and coronal alignment, for example. The recommendations and values provided by the functional planning data may be changed or edited manually.

Figure 10:
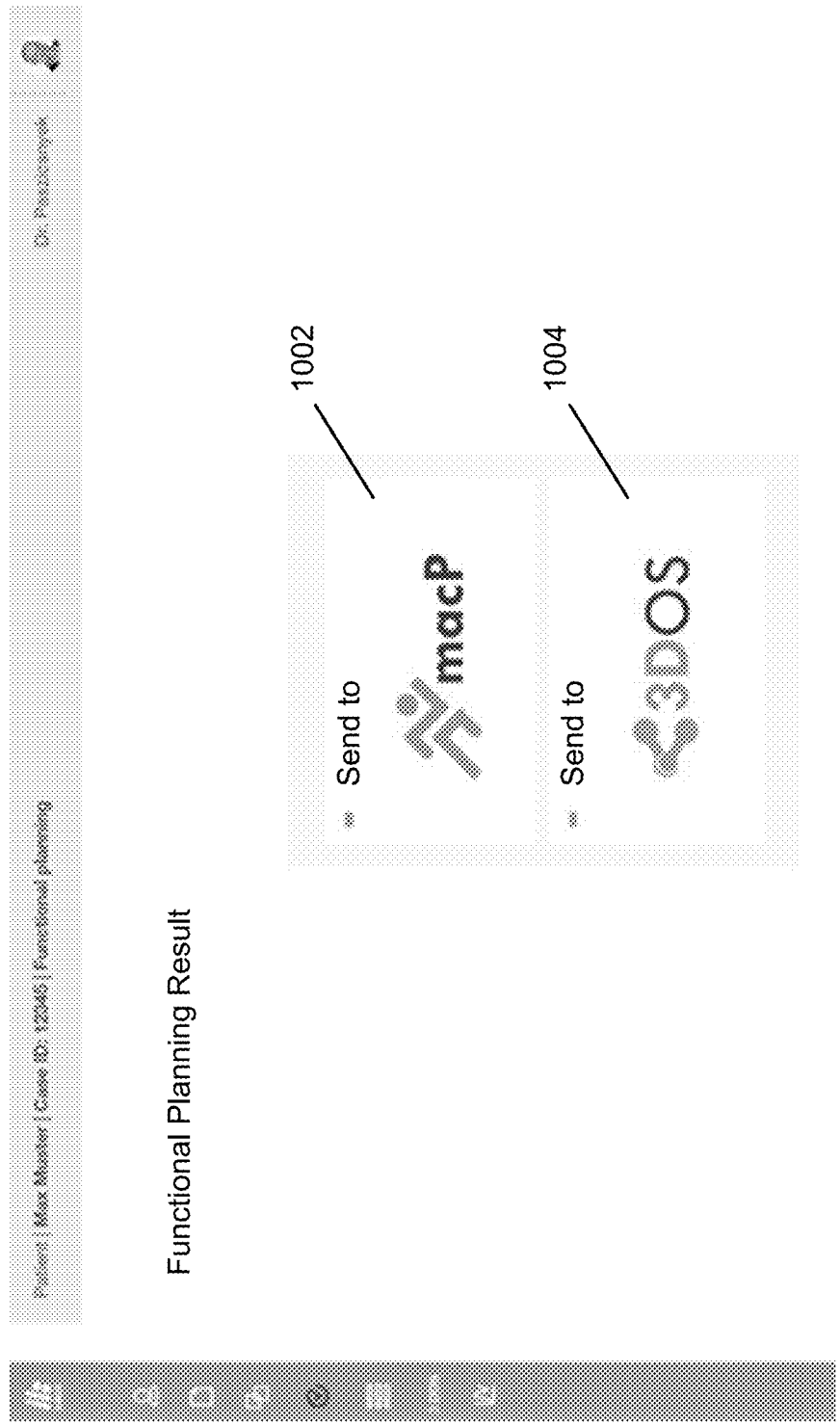

The functional planning data on the user interface may be confirmed and exported to a physiotherapy training system 1002 and a surgical orientation system 1004, as shown in FIG. 10. The physiotherapy training system 1002 may use the functional planning data to create training plans that concentrate on weak structures while protecting strong ones. The surgical orientation system 1004 may use the functionality planning data to calculate orientation of cutting planes and other surgical parameters for joint replacement.

The physiotherapy training system 1002 may use the measurement data from the functional planning data and compare the measurement data with reference data of measurements from healthy people with normal muscle function. Based on the comparison, the physiotherapy training system 1002 may generate a training plan. The physiotherapy training system 1002 may also continuously monitor training progress and strength/weakness of defined muscle structures. The physiotherapy training system 1002 may also record pain and passive range of motion.

Figure 11:
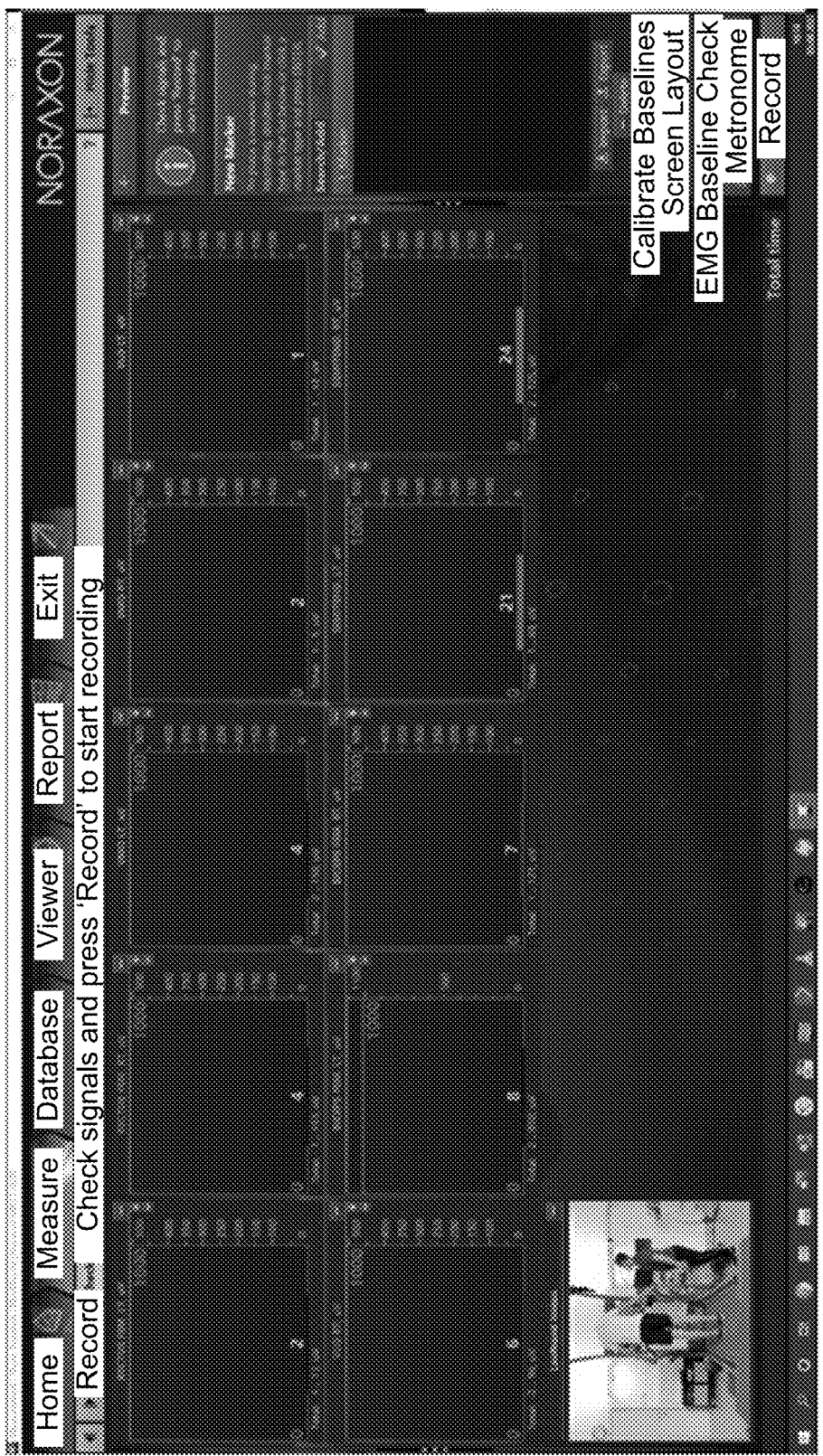
FIG. 11 illustrates an exemplary interface of a physiotherapy training system according to an embodiment of the present invention.

FIG. 11 presents an exemplary interface of a physiotherapy training system according to an embodiment of the present invention. The physiotherapy training system may receive signals from sensors and probes that are worn by a patient to generate testing results showing interoperability between different muscle structures as well as show which muscles are activated during movement or training. The physiotherapy training system may also identify weak structures to be trained more intensively and generate visual feedback training based on functional planning data received from, for example, a surgical planning and evaluation system.

FIGS. 1 through 11 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine-readable medium as part of a computer program product and is loaded into a computer system or other device or machine via a removable storage drive, hard drive, or communications interface. Computer programs (also called computer control logic or computer-readable program code) are stored in a main and/or secondary memory, and executed by one or more processors (controllers, or the like) to cause the one or more processors to perform the functions of the invention as described herein. In this document, the terms "machine readable medium," "computer-readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A method, in a data processing system comprising a processor and a memory, for determining rehabilitation treatment of a joint, the method comprising:
    communicatively connecting, by a computing device, to a plurality of sensors attached to an individual at muscles in a joint area, the plurality of sensors transmitting electrical signals generated by the muscle to the computing device;
    receiving, by the computing device, the electrical signals from the plurality of sensors;
    generating, by the computing device, initial measurement data by evaluating strength and activity level of the muscles based on the electrical signals;
    comparing, by the computing device, the initial measurement data with reference data, the reference data including measurements of healthy people with normal muscle function; and
    generating, by the computing device, a training plan based on the comparison.

2. The method of claim 1 further comprising measuring electrical signals generated by muscle cell activation.

3. The method of claim 1 wherein the plurality of sensors include sleeves with inwoven electromyographic sensors.

4. The method of claim 3 wherein the plurality of sensors include gyrosensors that are placed at a beginning and at an end of the sleeve.

5. The method of claim 1 wherein the plurality of sensors are placed according to a beginning and an end of defined muscles in a joint area.

6. The method of claim 1 wherein comparing the initial measurement data with reference data further comprises determining a target zone associated with the training plan.

7. The method of claim 1 wherein the training plan includes training procedures including progress and exercises to be performed along with explanations or descriptions.

8. The method of claim 1 wherein the training plan includes an exercise list and a target zone based on average data of a healthy cohort.

9. The method of claim 1 further comprising continuously adapting the training plan according to individual joint progress and abilities.

10. The method of claim 1 further comprising executing calibration procedures with the plurality of sensors by instructing through a user interface, a user to perform operations including at least one of moving forward and backward, flexing and extending a joint attached to the plurality of sensors, and rotating the joint.

11. A system for determining rehabilitation treatment of a joint, the system comprising:
    a processor; and
    a memory having executable instructions stored thereon that when executed by the processor cause the processor to:
        communicatively connect to a plurality of sensors attached to an individual at muscles in a joint area;
        receive electrical signals generated by the muscle from the plurality of sensors;
        generate initial measurement data by evaluating strength and activity level of the muscles based on the electrical signals;
        compare the initial measurement data with reference data, the reference data including measurements of healthy people with normal muscle function; and
        generate a training plan based on the comparison.

12. The system of claim 11 wherein the plurality of sensors measure electrical signals generated by muscle cell activation.

13. The system of claim 11 wherein the plurality of sensors include sleeves with inwoven electromyographic sensors.

14. The system of claim 13 wherein the plurality of sensors include gyrosensors that are placed at a beginning and at an end of the sleeve.

15. The system of claim 11 wherein the plurality of sensors are placed according to a beginning and an end of defined muscles in a joint area.

16. The system of claim 11 wherein the processor is further configured to determine a target zone associated with the training plan.

17. The system of claim 11 wherein the processor is further configured to execute calibration procedures with the plurality of sensors by instructing through a user interface, a user to perform operations including at least one of moving forward and backward, flexing and extending a joint attached to the plurality of sensors, and rotating the joint.

18. The system of claim 11 wherein the training plan includes an exercise list and a target zone based on average data of a healthy cohort.

19. The system of claim 11 wherein the processor is further configured to continuously adapting the training plan according to individual joint progress and abilities.

20. Non-transitory computer-readable media comprising program code that when executed by a programmable processor causes execution of a method for determining rehabilitation treatment of a joint, the computer-readable media comprising:
    computer program code for communicatively connecting a computing device to a plurality of sensors attached to an individual at muscles in a joint area, the plurality of sensors transmitting electrical signals generated by the muscle to the computing device;
    computer program code for receiving the electrical signals from the plurality of sensors;
    computer program code for generating initial measurement data by evaluating strength and activity level of the muscles based on the electrical signals;

computer program code for comparing the initial measurement data with reference data, the reference data including measurements of healthy people with normal muscle function; and computer program code for generating a training plan based on the comparison.

\* \* \* \* \*